United States Patent [19]

Joslin

[11] 4,455,140

[45] Jun. 19, 1984

[54] BODY FLUID COLLECTION DEVICE

[75] Inventor: Joel A. Joslin, Sunset Hills, Mo.

[73] Assignee: Sherwood Medical Company, St. Louis, Mo.

[21] Appl. No.: 332,062

[22] Filed: Dec. 18, 1981

[51] Int. Cl.³ .............................................. A61M 1/00
[52] U.S. Cl. .................................. 604/317; 604/318; 128/760
[58] Field of Search ................ 604/110, 153, 317–321, 604/327, 132–134, 181, 185; 128/760, 767, 768, 761; 222/541, 131, 398; 141/114, 329, 330; 150/0.5; 220/8

[56] References Cited

U.S. PATENT DOCUMENTS

| | | |
|---|---|---|
| 2,438,434 | 3/1948 | Friedman ............................ 220/8 |
| 3,329,298 | 7/1967 | Demas ................................. 220/8 |
| 3,625,216 | 12/1971 | Dannier, Jr. ....................... 604/321 |
| 3,648,698 | 3/1972 | Doherty ............................. 604/319 |
| 3,768,478 | 10/1973 | Fertik et al. ...................... 604/320 |
| 3,945,534 | 3/1976 | Ady ................................... 222/131 |
| 4,402,687 | 9/1983 | Denty ................................ 604/319 |

Primary Examiner—C. Fred Rosenbaum
Assistant Examiner—J. L. Kruter
Attorney, Agent, or Firm—Stanley N. Garber; Gregory E. Upchurch; William R. O'Meara

[57] ABSTRACT

A collapsible fluid collection device is provided which includes a container having upper and lower relatively movable telescopically disposed members, and sealing means for the container sealing the container against ambient air flowing between the members and into the container.

13 Claims, 9 Drawing Figures

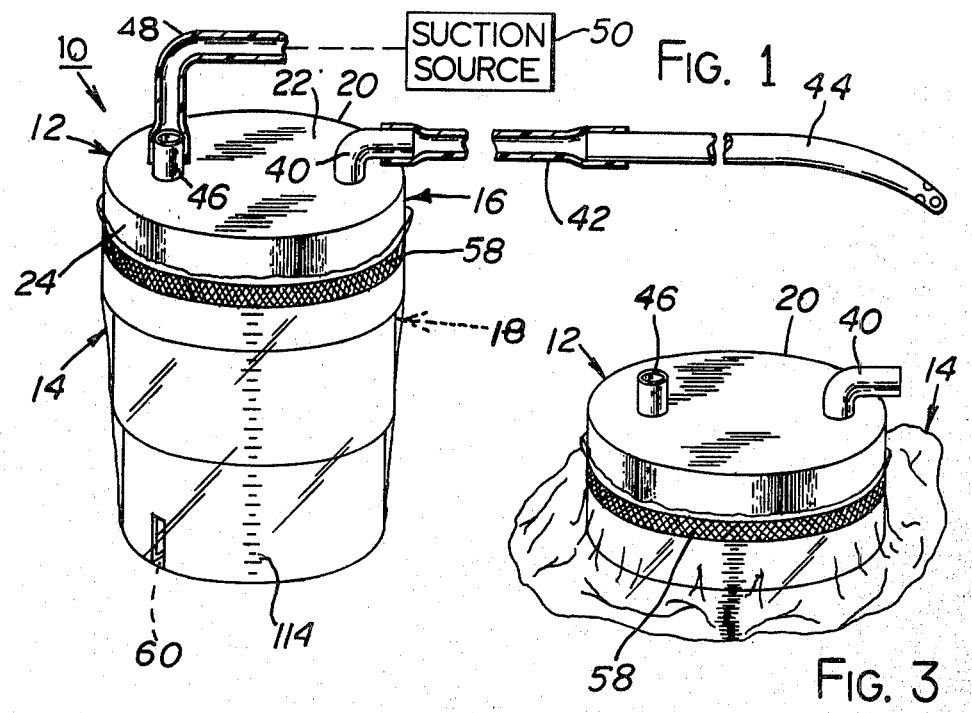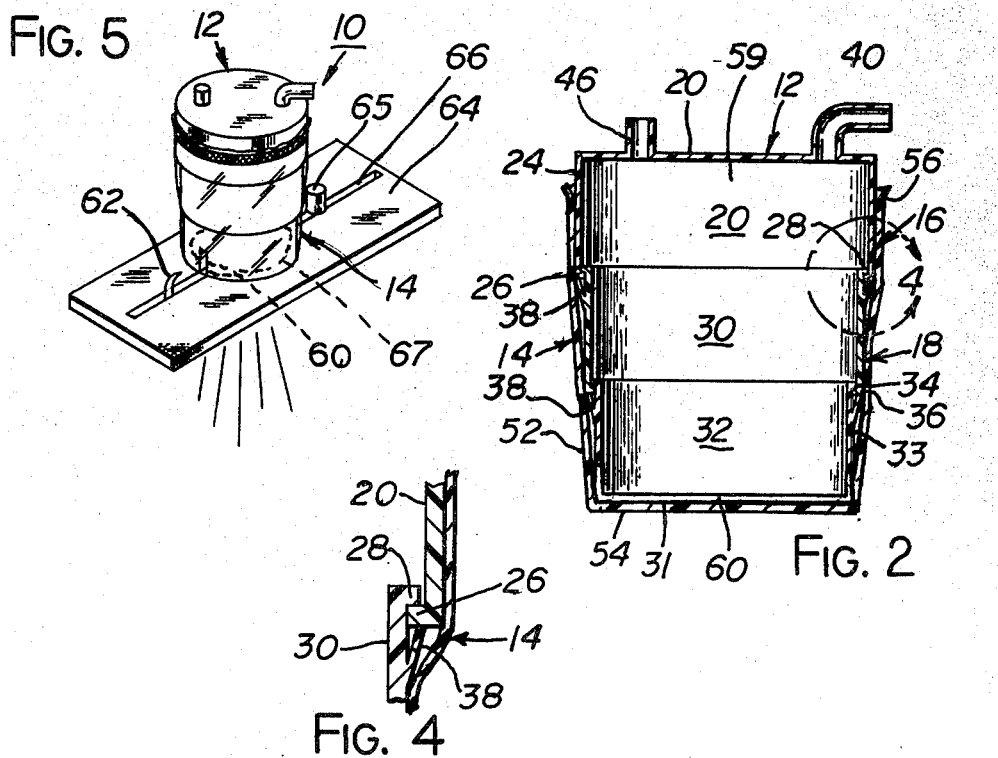

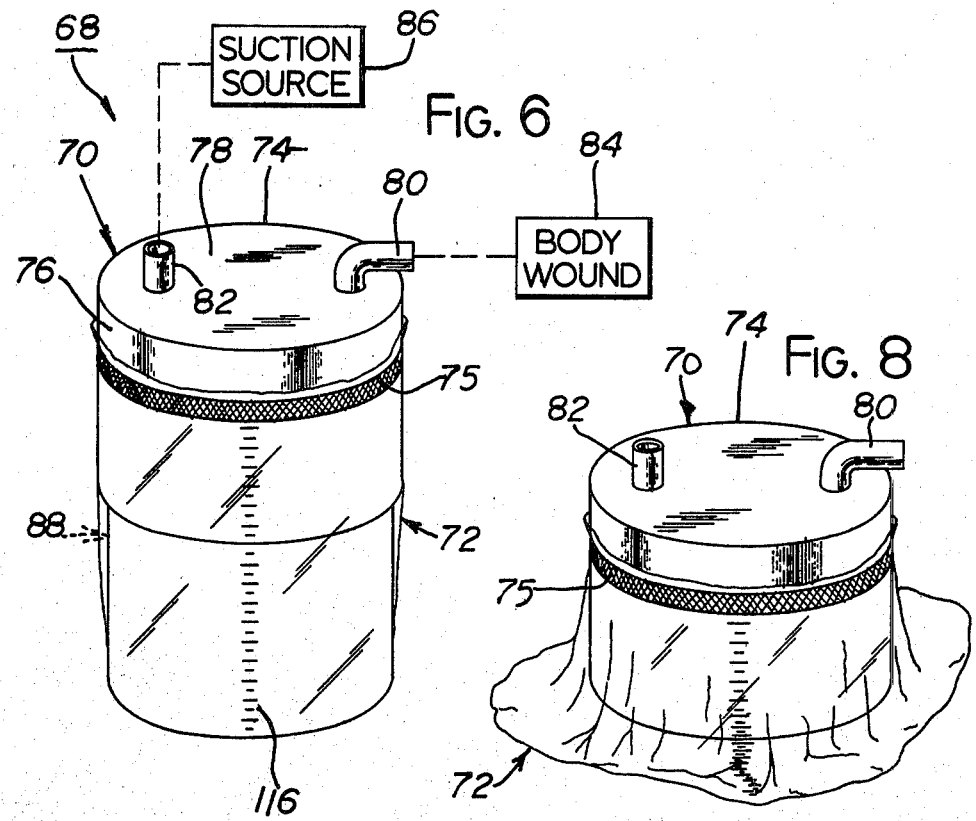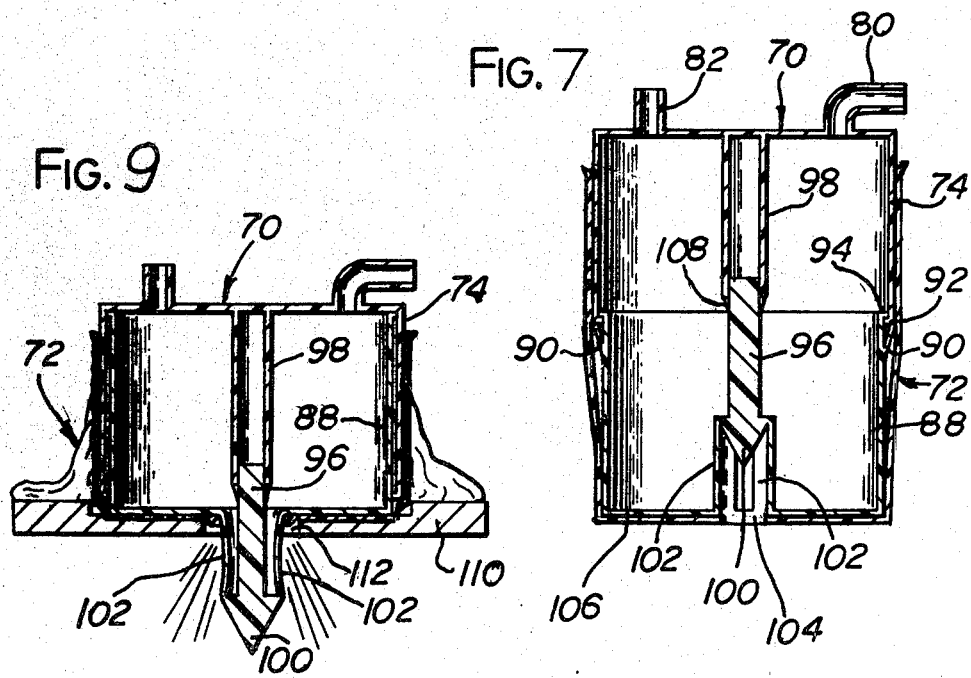

BODY FLUID COLLECTION DEVICE

DESCRIPTION

1. Technical Field

This invention relates to body fluid collection devices and more particularly to body fluid collection containers connectable between a source of negative pressure and a source of body fluid.

2. Background

Various types of containers or canisters which are connectable to a source of suction have been used for collecting body fluid from patients. Such suction containers may be used to drain body wounds such as chest wounds or surgical incisions. Generally, such containers are made of a rigid material such as a relatively rigid or hard plastic so that the container will maintain its shape or not collapse under vacuum. In some cases, a rigid container is provided with a flexible plastic liner such as disclosed in copending application Ser. No. 225,577 filed Jan. 16, 1981 now U.S. Pat. No. 4,346,711, and assigned to the same assignee as that of the present application. Such body fluid collection containers, for example, may be made large enough to hold 1200 to 2000 cubic centimeters of body fluid. One of the problems associated with the use of such rigid collection containers is that they require considerable storage space.

3. Disclosure of the Invention

An object of the present invention is to provide an improved fluid collection container for connection with a source of negative pressure, and which overcomes to a large extent, the above mentioned problem associated with the storage of collection containers.

Accordingly, a fluid collection device is provided which includes a collection container having a fluid inlet, a fluid outlet, and upper and lower sidewalls with relatively movable sidewall portions. The sidewall portions are relatively movable between a container collapsed condition and a container extended condition. The container is provided with sealing means to seal the interior of the device against the flow of ambient air between the sidewall portions and into the interior of the device.

These, as well as other objects and advantages of the present invention will become more apparent from the following detailed description and accompanying drawings.

BRIEF DESCRIPTION OF THE DRAWINGS

FIG. 1 is a perspective view of a fluid collection device in accordance with a preferred embodiment of the invention, the device being shown in use in its extended condition;

FIG. 2 is an elevational cross-sectional view of the collection device of FIG. 1;

FIG. 3 is a perspective view of the collection device of FIG. 1 in its collapsed or storage condition;

FIG. 4 is a cross-sectional view on an enlarged scale of a portion 4—4 of FIG. 2.

FIG. 5 is a perspective view on a reduced scale of the device of FIG. 1 on a container opening device;

FIG. 6 is a perspective view of a fluid collection device in accordance with a modified embodiment of the invention;

FIG. 7 is an elevational cross-sectional view of the device of FIG. 6;

FIG. 8 is a perspective view of the device of FIG. 6 but with the device in its collapsed or storage condition; and FIG. 9 is an elevational cross-sectional view of the device of FIG. 6 but in a collapsed condition for discharging collected fluid from the device.

DETAILED DESCRIPTION OF THE PREFERRED EMBODIMENT

Referring now to the drawings and particularly to FIGS. 1 and 2, collapsible fluid collection device 10 is shown in its extended condition and including a relatively rigid collapsible fluid container 12 and a seal 14 shown as a flexible sheet material member in the form of a bag for sealing the device against the flow of ambient air from the atmosphere into the interior of the container as will be discussed hereafter. The sealing bag 14 receives the container 12 and is sealingly connected to it. The container 12 is preferably made of a suitable transparent plastic that is relatively hard or rigid so that it will essentially maintain its shape and will not collapse due to the negative presures generally used. The container may be made, for example of a suitable relatively rigid, polyethylene, polystyrene, or polypropylene. The material of the sheet or bag 14 is preferably of a transparent, flexible and pliable plastic, such as thin flexible polyethylene, polypropylene, urethane, polyvinyl chloride, or other suitable thin flexible plastic material.

The container 12 includes relatively movable upper and lower portions 16 and 18, respectively. The container upper portion 16 includes a relatively rigid upper member 20 serving as a lid and having a circular upper end wall 22 and depending cylindrical sidewalls 24 integral with the upper end wall. As seen in FIG. 2 the bottom end of member 20 is open and is provided with a radially inwardly or internally extending, annular land or flange 26 which is shown engaged by a radially outwardly extending cooperative flange 28 at the upper end of an intermediate rigid container member 30 of the lower container portion 18. The member 30 is shown cylindrical and open at both ends.

The lower container portion 18 also includes a generally cup-shaped lower rigid member 32 open at the top and having a bottom wall 31 integral with a cylindrical sidewall 33. The member 32 has an upper outwardly extending flange 34 shown in cooperative engagement with an inwardly extending flange 36 at the lower end of the intermediate member 30.

The outer diameter of the three container members 20, 30 and 32 are made progressively smaller so that they are telescopically movable from a collapsed stored condition as shown in FIG. 3, to the extended container condition shown in FIGS. 1 and 2. They are dimensioned so that member 30 fits within member 20 and member 32 fits within member 30 in the collapsed condition, and when these members are relatively moved in a direction away from each other to the extended condition, the cooperating flanges serve to limit or stop the outward movement of the members as in FIG. 2. The flanges 28 and 34 engage the upper surfaces of flanges 26 and 36, respectively in the extended condition of container 12.

The intermediate member 30 and the lower member 32 are provided with a plurality of like, circumferentially spaced, resilient locking members 38. In FIG. 4 one such locking member 38 on member 30 is shown as an integral, normally outwardly extending tab engaging the bottom side of flange 26 of upper member 20 and preventing downward movement of member 20 relative to member 30. These locking members 38 on member 30 prevent inadvertent movement of member 30 into member 20, and the locking members 38 on member 32 engage the bottom of flange 36 on member 30 to prevent inadvertent movement of member 32 into member 30. Thus, the locking members 38 and associated flanges on the members lock the relatively movable sidewalls of the containers 12 in the extended condition (FIGS. 1 and 2), the condition in which the device 10 is used to collect fluid.

The locking members 38 are shown formed of the same plastic material as the container members and relatively thin and therefore sufficiently resilient to allow the flanges 26 and 36 to flatten them against the container, and pass over and move past the locking members during movement of the container members 20, 30 and 32 from their collapsed storage condition shown in FIG. 3 to the extended condition shown in FIG. 2. The container members and locking members are, of course, flexible enough to allow the members to be manually assembled together during manufacture into the collapsed condition for packaging.

The upper member 20 is provided with a fluid inlet 40 shown connected to tubing 42 which is shown connecting with a catheter 44 adapted to be connected with a source of body drainage fluid such as a chest wound. The member 20 also is shown provided with a fluid or gas outlet 46 shown connected to tubing 48 which, in turn, is connected to a source of negative pressure or suction source 50. Both the inlet 40 and outlet 46 are shown as tubular tube connectors extending from and integrally formed with the upper end wall 22 of the upper member 20.

The plastic sheet material member or bag 14 is provided with generally cylindrical sidewalls 52 and a bottom wall 54 integrally connected with the sidewalls 52. The bag 14 is closed except that it has an upper open end 56. The upper end 56 is sealingly secured to the upper container member 20 entirely around the container. This may be accomplished by adhesive, solvent bonding, or by welding, depending upon the types of materials employed. In FIGS. 1 and 3 an annular weld or seal is indicated at 58. In this way, substantially no ambient gas, such as air, can pass out of the interior of the device 10 to the atmosphere or into the device from the atmosphere except by means of the inlet and outlet tube connectors 40 and 46. In other words, ambient air cannot pass between the relatively slidable sidewall portions or members of the container to the interior of the container or chamber, indicated at 59 in FIG. 3.

The bottom member 32 is also shown provided with an opening 60 in the form of a slot extending diametrically across the bottom wall 31 and a limited distance upwardly in the sidewall 33 at diametrically opposite sides of the member. The slot 60 allows a cutting member 62, shown in FIG. 5, to pass through the slot and cut open the bottom of the bag 14 for the purpose of discharging collected body fluid and/or other drainage matter into a suitable receptacle (not shown), as will be further discussed. This may be done prior to the disposal of a used collection device 10.

The collapsible fluid collection device 10 is normally packaged and stored in its collapsed condition as shown in FIG. 3. It will be apparent that its storage volume is substantially less than its volume when extended for use as in FIGS. 1 and 2. For example, in its collapsed or storage condition, the volume of the device is about 1/3 of the volume that it has when extended for use. This greatly reduces the storage space required when compared to conventional non-collapsible suction containers of the same volume or fluid capacity.

In use, the collapsed device 10 is removed from storage and extended by moving the members 30 and 32 outwardly away from member 20 until they are locked into the position shown in FIG. 2 by locking members 38 and cooperating flanges on the members. The inlet 40 is connected by tube 42 and catheter 44 with a source of fluid to be collected, such as a body wound of a patient. The outlet 46 is connected to a source of suction 50 by tube 48. Drainage fluid flows from the body wound or incision into the interior or collection chamber 59 of the container 12 and bag 14. The container members 20, 30 and 32 maintain the bag open when a suitable negative pressure is applied through the outlet 46.

After the device 10 is filled to a desired level, the device may be disconnected from the negative source and patient and placed on a table 64 shown in FIG. 5. The slot 60 is aligned with cutter 62 and the cutter is moved such as by a connecting handle 65 through a slot 66 in the table to open the bottom of the bag 14 and allow collected fluid to flow from the device 10 through an opening 67 in the table to a suitable receptacle under the table. The device 10 may then be discarded.

Referring now to FIGS. 6 through 9, a modified collapsible fluid collection device 68 is shown including a rigid but collapsible container 70 received in a pliable plastic sheet material member 72 shown in the form of a bag. The bag 72 is open only at the top and is sealingly secured to an upper container portion 74 by a weld or seal 75. The upper container portion includes a rigid member having cylindrical sidewalls 76 to which the bag is connected and an integral upper wall 78. Upper wall 78 has inlet and outlet tube connectors 80 and 82 shown respectively diagrammatically connected to a body wound 84 and a source of suction 86.

The container 70 has a lower portion 88 which includes a single relatively rigid member having a plurality locking members 90 (FIG. 7) which are similar to locking members 38 in FIG. 4. The upper and lower members 74 and 88 are cup-shaped and have cooperating inwardly and outwardly extending annular flanges 92 and 94, respectively, which limit the relative outward movement of the members to the extended condition shown in FIG. 7. In FIG. 8, the lower member 88 is disposed in the upper member 74 so that the container 20 is in its collapsed storage condition.

The lower member 88 is provided with a plastic sheet or bag penetrating element 96, and the upper member 74 is provided with a penetrating element receiving and actuating element 98. The penetrating element 96 is elongate and has a bag piercing point 100 and a plurality, such as three, resilient and flexible connecting fingers 102 (two shown in FIG. 7) integrally connected to the point 100. The fingers 102 normally space the point 100 from a bottom opening 104 in the bottom wall 106 of the container member 88.

The actuating element 98 is cylindrical and slidingly receives the bag penetrating element 96 when the device 68 is in the original storage, collapsed condition shown in FIG. 8. In this condition the lower member 88 is disposed in telescoping relating with upper member 74 and the point 100 is held spaced from opening 104 by fingers 102. When the members 74 and 88 are moved apart toward the extended condition, the element 96 and 98 move relative to each other to the position shown in FIG. 7. The penetrating element 96 is provided with circumferentially spaced, integral resilient locking elements 108 that are similar to locking members 90 so that when the element 96 reaches the extended position shown in FIG. 7, the locking elements 108 become free of the walls of element 98 and engage the bottom end of element 98. Thus, the bag penetrating element 96 is locked in position and cannot return within element 98 under normal operation of the device.

In use, the packaged and stored device 68 is removed from its package and extended to its condition of FIG. 7. The device 68 may then be employed as in FIG. 1 to collect drainage fluid from the body wound 84. After a desired amount of fluid is collected, the device 68 is detached from the patient and suction source 86 and placed, as shown in FIG. 9, on a table 110 which has an opening 112.

With the opening 104 of member 88 in registration with the table opening as in FIG. 9, the upper member 74 is pushed downwardly driving the point 100 of the bag penetrating member 96 through openings 104 and 112 to pierce the bag 72 and allow collected drainage fluid to flow through these openings and between the fingers into a suitable recepticle (not shown). As the member 96 moves downwardly, the resilient fingers 102 bend inwardly and downwardly with the member 96 passing between the fingers. After emptying the fluid collection device 68, it may be suitably discarded.

The collection device 68 is collapsible to about one-half its extended volume so that the storage space required for such devices is about one-half of that required by a conventional non-collapsible container of similar capacity.

The containers 12 and 70 are shown provided with calibration marks 114 and 116, respectively.

If desired, the bottom members of the containers 12 and 20 may be completely closed, that is, without a discharge opening. In such case, the sheet material 14 or 72 may simply be a cylindrical piece of plastic sheet material sealed at the top to the upper member as shown in the drawings, and similarly sealed at the bottom to the sidewall of the lower container member. The bag or sheet material should, of course, be long enough to permit the member to be moved to the extended condition. In such cases, the sheet material extends over the junctures or abutting flanges of the adjacent container members to prevent air from flowing through the juctures to the interior of the container.

In some cases, the pliable plastic sheet material or bag may be disposed inside the container and used as a liner or fluid collection bag. The plastic material or bag should, of course, be connected inside the container such that it does not collapse inwardly when a negative pressure is applied to the outlet.

As various changes could be made in the above constructions without departing from the scope of the invention, it is intended that all matter contained in the above description and apparatus shown in the accompanying drawing shall be interpreted as illustrative and not in a limiting sense.

I claim:

1. A body fluid collection container assembly for fluid connection between a source of negative pressure and a source of fluid to be collected comprising a cover, a telescopically collapsible container including an upper portion including an upper member of rigid material, and a lower portion including a lower member of rigid material, said upper and lower portions being telescopingly movable relative to each other from a collapsed container condition in which the internal volume of the assembly is relatively small to a maximum extended container condition in which the internal volume of the assembly is larger than when collapsed, locking means on said container for locking said upper and lower portions in the extended condition including abutting surfaces at the juncture of said upper and lower portions when in the maximum extended container, fluid inlet means connected to said upper member for connecting a source of fluid with the interior of the assembly, suction outlet means on said cover for connecting the interior of the assembly with a source of negative pressure, and sealing means of flexible sheet material sealingly connected to said container for sealing the interior of the assembly against the flow of air from the atmosphere between said telescoping portions and into the interior of the assembly, said sealing means having portions thereof extending across said juncture to prevent air therethrough to the interior of the assembly.

2. The device of claim 1 wherein said locking means allows movement of said lower portion relative to said upper portion in a direction to place said container in the extended container condition but prevents movement thereof in a direction from the extended container condition toward the collapsed container condition.

3. The device of claim 1 wherein said container is of a relatively hard plastic and substantially non-deformable when the container is connected to a negative source in use, and said sheet material is of a pliable plastic, and wherein said sheet material is in the form of a bag having a single opening at the upper end thereof and includes sidewalls and a bottom wall integral with said sidewalls, said upper end being sealingly connected to said upper member so that said opening is sealingly closed by said upper member and whereby when said container is in the extended condition in use fluid can flow into said container only through said fluid inlet means.

4. The device of claim 1 wherein said lower portion of said container also includes an intermediate member of relatively rigid material telescopingly movable relative to said upper and lower members.

5. The device of claim 1 wherein said lower portion has a bottom wall with an opening therein for the discharge of collected fluid from said container, and a portion of said sealing means closes said opening.

6. The device of claim 1, 4 or 5 wherein said sheet material extends over the juncture of said upper and lower portions to prevent ambient air from flowing through said juncture.

7. A body fluid collection container assembly for fluid connection between a source of negative pressure and a source of fluid to be collected comprising a container including a cover, an upper portion including an upper member of rigid material, and a lower portion including a lower member of rigid material, said upper and lower portions telescopingly movable relative to each other from a collapsed container condition in which the internal volume of the assembly is relatively small to an extended container condition in which the internal volume of the assembly is larger than when collapsed, fluid inlet means connected to said upper member for connecting a source of fluid with the interior of the assembly, suction outlet means on said upper member for connecting the interior of the assembly with a source of negative pressure, and a sealing member of flexible sheet material sealingly connected to said container to seal the interior of the assembly against the flow of air from the atmosphere between said telescoping members and into the interior of the assembly, said bottom member having a bottom wall and sidewalls with a slot extending across said bottom wall and upwardly into said sidewalls on opposed sides of said bottom member, said slot being adapted to receive a cutting element movable through said slot to open the bottom of said sealing member for discharging fluid from said container.

8. A body fluid collection container assembly for fluid connection between a source of negative pressure and a source of fluid to be collected comprising a container including an upper portion including an upper member of rigid material, and a lower portion including a lower member of rigid material, said upper and lower portions being telescopingly movable relative to each other from a collapsed container condition in which the internal volume of the assembly is relatively small to an extended container condition in which the internal volume of the assembly is larger than when collapsed, fluid inlet means connected to said upper member for connecting a source of fluid with the interior of the assembly, suction outlet means on said upper member for connecting the interior of the assembly with a source of negative pressure, and a sealing member of flexible sheet material sealingly connected to said container to seal the interior of the assembly against the flow of air from the atmosphere between said telescoping members and into the interior of the assembly, said sheet material being disposed externally to said container.

9. The device of claim 1 or 8 wherein said locking means includes resilient tab means on one of said upper and lower portions allowing relative movement of said portions until they are in the extended condition of the container, said resilient tab means of said one portion resiliently engaging the other portion in the extended position of the container to prevent movement of said portions to the collapsed container condition.

10. A body fluid collection container assembly for fluid connection between a source of negative pressure and a source of fluid to be collected comprising a container including assembly upper portion including an upper member of rigid material, and a lower portion including a lower member of rigid material, said upper and lower portions being telescopingly movable relative to each other from a collapsed container condition in which the internal volume of the assembly is relatively small to an extended container condition in which the internal volume of the assembly is larger than when collapsed, fluid inlet means connected to said upper member for connecting a source of fluid with the interior of the assembly, suction outlet means on said upper member for connecting the interior of the assembly with a source of negative pressure, and a sealing member of flexible sheet material sealingly connected to said container to seal the interior of the assembly against the flow of air from the atmosphere between said telescoping members and into the interior of the assembly, said sealing member comprising a plastic bag.

11. The device of claim 10 wherein said bag has a single opening sealingly connected to the exterior of said upper container portion and receiving said lower container portion.

12. The device of claim 11 wherein said bag is formed of a pliable plastic material.

13. The device of claim 1, 10, 11 or 12 wherein said sheet material is disposed externally to said container.

* * * * *